United States Patent [19]

Denard

[11] Patent Number: 5,087,252
[45] Date of Patent: Feb. 11, 1992

[54] URINARY CATHETER FOR HUMAN MALES

[76] Inventor: Ruthie Denard, 74 Garfield, Apt. 305, Detroit, Mich. 48201

[21] Appl. No.: 553,613

[22] Filed: Jul. 18, 1990

[51] Int. Cl.[5] ................................................. A61F 5/44
[52] U.S. Cl. ..................................... 604/346; 604/349
[58] Field of Search ................. 128/760, 768; 604/49, 604/54, 327, 328, 346, 347, 349, 351, 50, 34, 280; 4/144.1

[56] References Cited

U.S. PATENT DOCUMENTS

| | | | |
|---|---|---|---|
| 2,007,069 | 7/1935 | Berg | 604/276 |
| 4,205,690 | 6/1980 | Layton | 128/768 |
| 4,449,971 | 5/1982 | Cawood | 604/328 |
| 4,710,169 | 12/1987 | Christopher | 604/349 |
| 4,769,018 | 9/1988 | Wilson | 604/328 |
| 4,810,247 | 3/1989 | Glassman | 604/174 |
| 4,820,263 | 4/1989 | Speuak et al. | 128/798 |
| 4,904,245 | 2/1990 | Chen et al. | 604/248 |

Primary Examiner—Randall L. Green
Assistant Examiner—R. Clarke
Attorney, Agent, or Firm—Dykema Gossett

[57] ABSTRACT

The urinary catheter is insertable into the urinary bladder of a human male through the penis and uretha for the withdrawal of urine from the urinary bladder. The catheter comprises an elongated tubular flexible element having a pair of end portions, with the first end portion constituting the leading and of the catheter which is introduced into the urinary bladder. One or more openings are provided in the first end portion for delivering urine from the urinary bladder into the tubular flexible element. The other end portion of the tubular flexible element constitutes the trailing end of the catheter and is not insertable into the penis. Valve means are provided in the other end portion for opening and closing the tubular element to permit withdrawal of urine from the tubular element or collection of urine within the tubular element. A support strap is provided for the tubular element. The strap has an adhesive surface adapted for securing the strap to the penis for preventing the accidental withdrawal of the tubular element from the penis and urethra.

7 Claims, 2 Drawing Sheets

URINARY CATHETER FOR HUMAN MALES

BACKGROUND OF THE INVENTION

1. Field of the Invention

The present invention relates to urine collection devices for human males. Such devices are needed not only by incontinent male individuals, but also by those who, by virtue of their particular circumstances, are precluded from using ordinary restroom facilities for either short or extended periods of time. Several examples of the foregoing include those who are geriatric males, chronically ill or are undergoing post-operative treatment in bed. Other examples include males who are incapacitated, disoriented or have a continuous drip as well as those whose occupations demand that they remain or duty and/or continuously wear special protective clothing for extending periods of time. Regardless of the cause of the urinary condition or problem, such conditions may present emotional, social and/or psychological problems in the human male.

2. Description of the Prior Art

My earlier patent, U.S. Pat. No. 4,387,726, issued June 14, 1983 entitled "Disposable Urine Collection Device for Human Males" discloses an external types of a device which is designed to keep the individual clean, dry and comfortable so that he may function to his full capacity without restraint. Other types of disposable urethra catheters are shown in U.S. Pat. No. 4,246,901 entiled "Urine Collection Device", Inventors, Robert A. Frosch et al and in U.S. Pat. No. 4,246,909 entitled "Disposable Urethra Catheter Assembly", Inventors, Yeongchi Wu et al, each patent dated Jan. 27, 1981. The prior art device used by males are not generally comfortable and leakage from the devices often occur. In addition, such known devices interfere with the user's freedom of movement and ability to assume various postures. Also, such devices limit the user's choice of clothing.

SUMMARY OF THE INVENTION

The present invention provides a urinary catheter for human males which permits the human male to function to his full capabilities without restraint and in particular is ideal for the male who has problem with the urinary tract regardless of the cause. The urinary catheter of the present invention may be referred to as a "walking catheter" since it permits a male with urinary tract problems or conditions to function normally without having to worry about uncontrolled urine leakage.

Thus it is a feature of the present invention to provide a urinary catheter insertable into the urinary bladder of a human male through the penis and urethra for the withdrawal of urine from the urinary bladder. Such catheter may also be referred to as an internal catheter and comprises an elongated tubular flexible element having a pair of end portions. The first end portion of the flexible element constitutes the leading end of the catheter and is the end portion which is introduced into the urinary bladder through the penis. One or more openings are provided in the first end portion for delivering urine from the urinary bladder into the tubular flexible element. The other end portion of the flexible element constitutes the trailing end of the catheter which is the portion which is not insertable into the penis. Valve means is provided in the other end portion for opening and closing the elongated element to permit withdrawal of urine from the element or collection of urine within the element.

Another feature of the present invention is to provide a catheter wherein the first end portion has a plurality of openings therein at longitudinally and radially spaced areas thereof to permit the flow of urine from the bladder into the tubular element.

Still another feature of the present invention is to provide a catheter of the aforementioned type wherein the first end portion has an opening in the end wall thereof to permit the flow of urine from the bladder into the tubular element.

A further feature of the present invention is to provide a catheter of the aforementioned type wherein a closure cap is provided on the other end of the flexible element in which the valve means is located. With such construction, the valve means is an on-off type valve which can be operated by the male user to permit periodic drainage of the flexible element when required.

A still further feature of the present invention is to provide a catheter of the aforementioned type wherein the on-off type valve has a valve element mounted within the closure cap, with the valve element having a passage therein which, when in one position, permits the urine to drain form the flexible tube and which, when in another position, blocks the flow of urine from the flexible element.

Another feature of the present invention is to provide a catheter of the aforementioned type wherein the flexible element and the closure cap are made from plastic material.

Still another feature of the present invention is to provide a catheter of the aforementioned type wherein a support strap is provided and through which the flexible element extends. The support strap has a pair of arms, each arm having an adhesive surface for securing the arms to the penis or to the sensitive scrotal area of the human male to prevent the accidental withdrawal of the tubular element from the human male.

A further feature of the present invention is to provide a catheter of the aforementioned type wherein an antiseptic or medically treated disc is carried by the support strap, surrounds the tubular element and is engageable with the head of the penis for assisting in preventing germs from entering the human male through the penis.

A final feature of the present invention is to provide a disposable internal catheter that is concisely constructed for incontinency of urine in the human male and is designed to keep the individual clean, dry and comfortable so that he may function to his full capacity without restraint.

DETAILED DESCRIPTION OF THE PREFERRED EMBODIMENT

Figure 2:
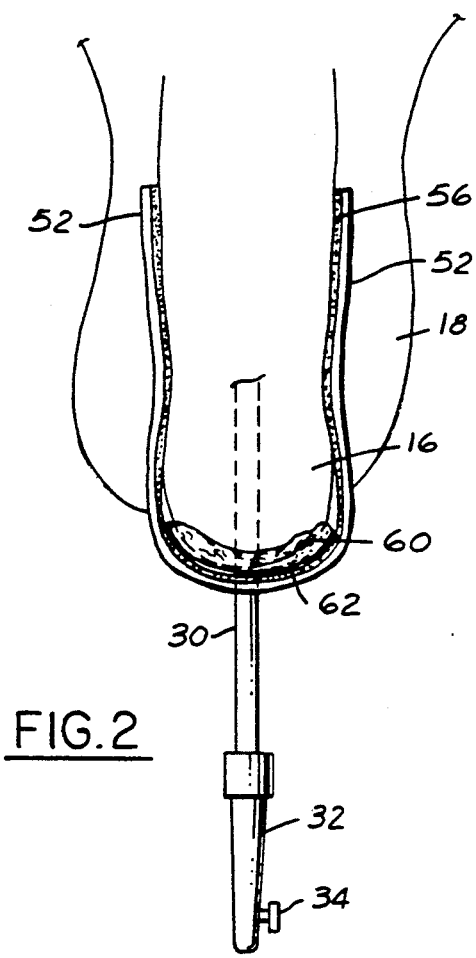
FIG. 2 is a fragmentary view of the internal catheter showing the manner in which the catheter is held in place with reference to the human male anatomy by means of support straps.
Figure 3:
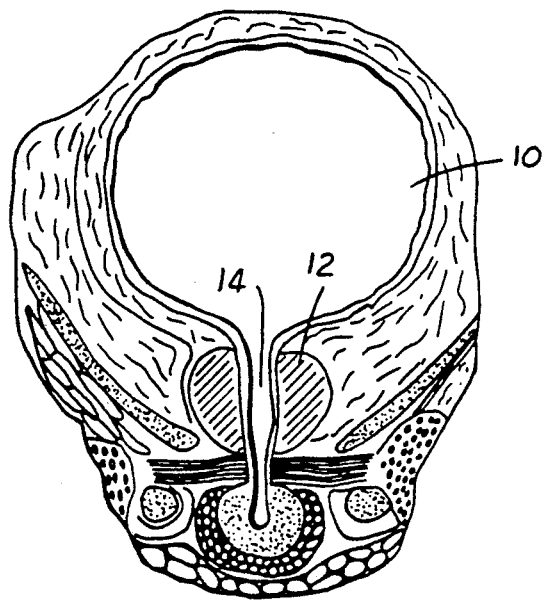
FIG. 3 is a fragmentary pictorial view of a human male showing the bladder and the prostate gland.
Figure 4:
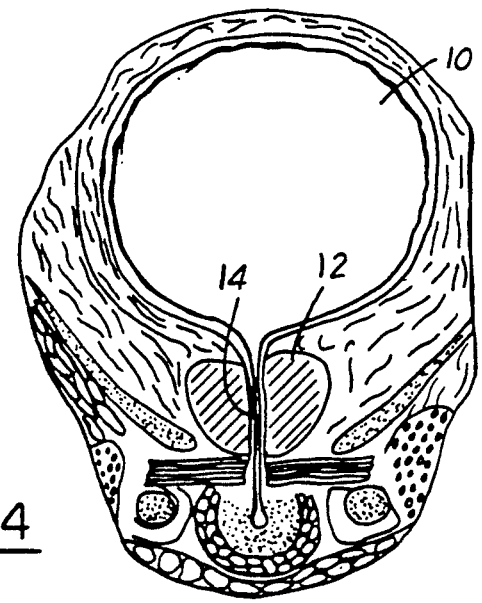
FIG. 4 is a view similar to the FIG. 3 but showing an enlarged prostate which constricts the urethra, causing retention.

FIGS. 2-6 inclusive illustrate portions of a human male, including the urinary bladder 10, prostate gland 12, the urethral duct 14, penis 16 and the testicle 18. The prostate gland 12 is shown in FIG. 3 so as to not restrict the urethral duct 14. In FIG. 4, the prostate gland 12 is enlarged so as to constrict the urethra or duct 14.

Figure 1:
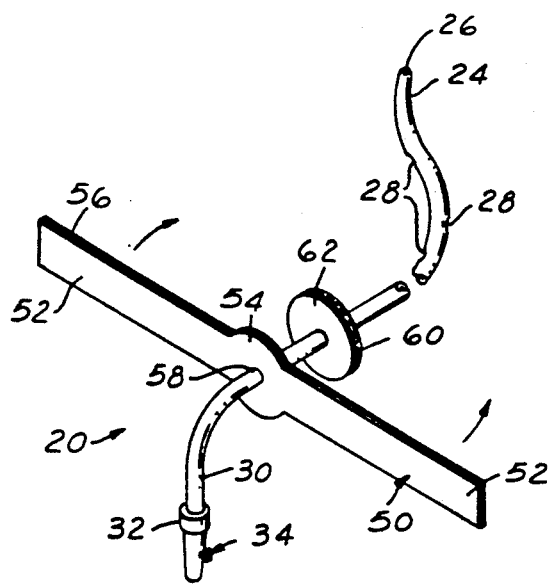
FIG. 1 is a fragmentary perspective view of the internal catheter forming the subject matter of the present invention.
Figure 5:
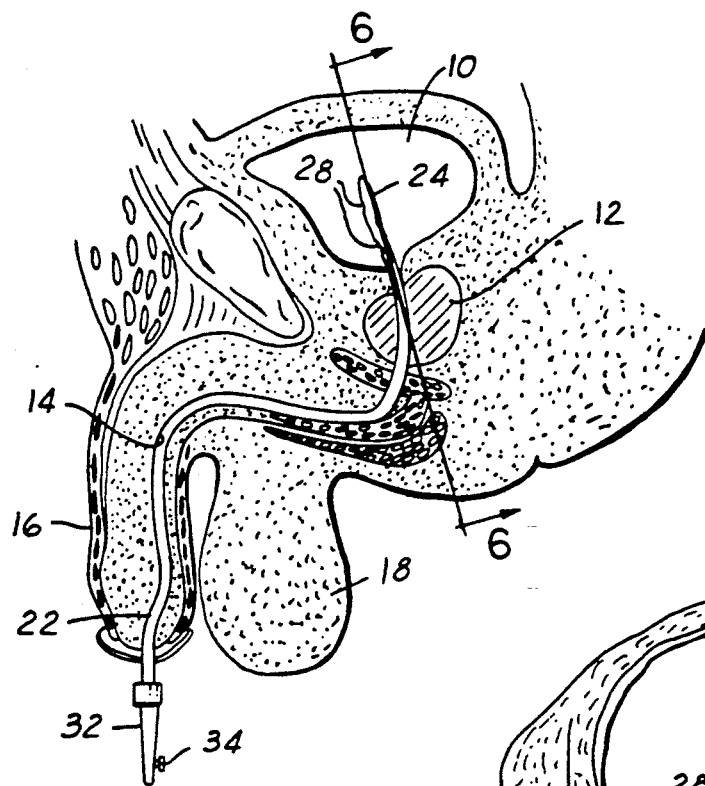
FIG. 5 is another pictorial view of the human male, showing the internal catheter inserted through the penis and urethra into the urinary bladder.
Figure 6:
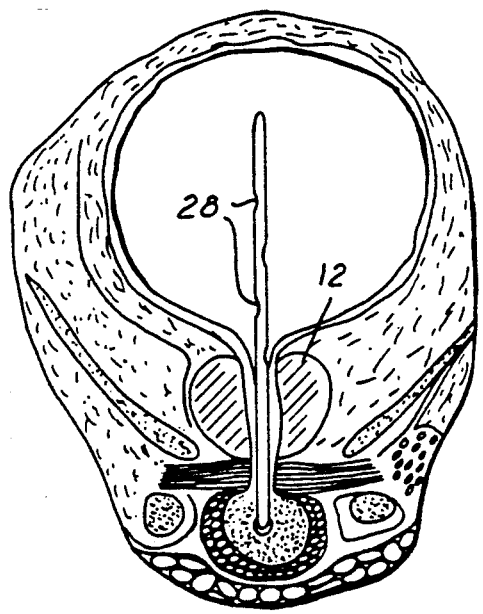
FIG. 6 is a sectional view taken on the line 6—6 of FIG. 5.
Figure 7:
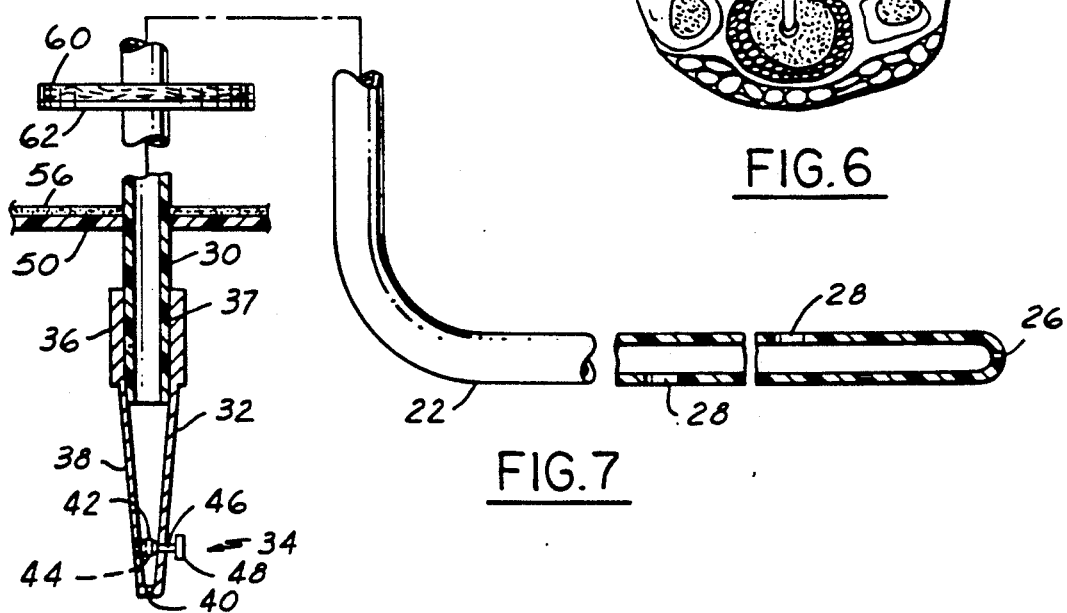
FIG. 7 is a fragmentary, partial sectional view through the internal catheter.

The urinary catheter 20 comprises an elongated tubular flexible element or tube 22 made from a plastic material such as a medically approved plastic now used in hospitals. The flexible tubular element 22 has a length of approximately 11 to 16 inches and is made from a clear plastic material. The tubular element 22 has a leading end portion 24 which is provided with an opening 26 in the tip or end wall thereof. In addition the leading end portion 24 is provided with a plurality of longitudinally and radially spaced openings 28 as shown in FIGS. 1, 5 and 6.

The other end portion 30 of the tubular element 22 is provided with a closure cap 32 having mounted thereon and therein an on-off type valve 34. The valve 34 has two positions only one open to permit drainage of the urine and one closed to permit collection of the urine within the tube 22. The cap 32 has an end portion or collar 36 which is sleeved over the trailing end portion 37 of the flexible tube 22 and in effect constitutes a part thereof. The closrue cap 32 includes a tapered or funnel portion 38 having at the terminal end thereof an opening 40 through which urine may drain. In addition, the closure cap 32 carries the on-off valve 34 which includes a valve element 42 having a through passage 44 provided therein. In addition a shaft 46 is connected to the valve element 42. The shaft 46 extends through the wall of the closure cap 32 and is provided thereon an externally mounted operating handle 48.

The urinary catheter 20 is insertable into the urinary bladder 10 of a human male through the penis 16 and the urethra 14 for the collection and the withdrawal of urine from the elongated tubular flexible element 22. The end portion 24 constitutes the leading end portion of the catheter 20 and is introduced into the urinary bladder where the openings 28 are positioned to receive the urine from the bladder 10.

The other end portion 30, sometime referred to as a trailing end portion of the flexible element 22 carries the valve means 34 exteriorly of the anatomy of the human male. Thus, the trailing end portion of the catheter is not inserted into the human male, but rather is positioned in close proximity to the head of the penis 16 as shown in FIG. 5 so that the user may function as normally as possible.

The urinary catheter 20 is provided with a support strap 50 having a pair of arms 52 on opposite sides of a center enlargement 54. The interface of the strap 50 is provided with a medically acceptable adhesive layer 56. The center section 54 has an opening 58 through which the tubular element 22 extends as shown in FIG. 1. In order to prevent or to assist in preventing infections in the urinary duct 14 and elsewhere within the human male, a medically treated disc or antiseptic type element 60 is provided on a support element 62 through which the tubular element 22 extends. The support element 62 is secured to the strap 50 by the adhesive 56. The strap 50 is flexible and is also made of a plastic material. After the flexible element 22 has been inserted into the human male as shown in FIG. 5, removable strips, not shown, provided over the adhesive surface 56 are removed so that the strap 50 may be folded into U-shape configuration, with the arms 52 engaging and being secured to the skin of the penis by means of the adhesive 56 as shown in FIG. 2. The strap 50 is to assist in preventing the accidental withdrawal of the tubular element 22 from the penis and the urethra. The strap 50 holds the antiseptic or medically treated disc 62 in contact with the head of the penis as shown in FIG. 2.

The internal catheter 20 may be comfortably worn by the male user. When the tubular elemtn 22 is filled, the human male may use available public or private accommodations and eliminate the urine from the tube 22 by opening the valve 34. Once this particular operation has been completed, the user closes the valve 34 and resumes normal activities.

The antiseptic disc 60 may be made from a soft cloth material or fabric which is treated with an antibacterial agent. The purpose of the antiseptic disc is to prevent the germs from entering the interior of the human male.

The urinary catheter disclosed herein may be described as a "walking catheter" since only a small portion thereof protrudes beyond the head of the penis. Thus, a person may comfortably wear the catheter and function as normally as possible.

The urinary catheter described herein will permit a human male to be clean, dry and comfortable so that he may function as normally as possible thus continuing to provide a sense of well being. The plastic material may be vinyl or other conventional medically acceptable types used with medical devices. The sticky or adhesive surfaces of the strap may be provided with peal off covers which are removed prior to use.

It should be understood that other types of on-off valves 34 may be used in the closure cap 32 to permit drainage of the catheter when in one position and closing of the catheter to collect the urine when in the other position.

What I claim is:

1. A urinary catheter insertable into the urinary bladder of a human male through the penis and urethra for the withdrawal of urine from the urinary bladder comprising an elongated tubular flexible element having a pair of end portions, the first end portion constituting the leading end of the catheter which is introduced into the urinary bladder, one or more openings provided in said first end portion delivering urine from the urinary bladder into the tubular flexible element, the other end portion of said tubular flexible element constituting the trailing end of the catheter which is not insertable into the penis, and valve means provided between said end portions for opening and closing the tubular element to permit withdrawal of urine from the tubular element or collection of urine within the tubular element, said tubular flexible element extending through a center portion of a support strap, said support strap having a pair of arms with each arm having an adhesive for securing said arm to a patient to assist in preventing accidental withdrawal of the flexible tubular element; and said valve means is an on-off type valve having a valve element with a passage therein, a shaft connected to said valve element, and an operating handle secured to said shaft for rotating same thereby opening or closing said valve means.

2. The catheter as recited in claim 1 wherein said first end portion has a plurality of openings therein at longitudinally and radially spaced areas thereof.

3. The catheter as recited in claim 2 wherein said first end portion has an opening in the end wall thereof.

4. The catheter as recited in claim 1 wherein a closure cap is provided on said other end of said flexible element and in which said valve means is located.

5. The catheter as recited in claim 1 in which the flexible element and the closure cap are made from plastic.

6. The catheter as recited in claim 1 wherein said flexible element extends through the center portion of said support strap; and a medically treated disc surrounding the tubular element and engageable with the head of the penis for assisting in the prevention of infections in the human male.

7. A urinary catheter insertable into the urinary bladder of a human male through the penis and urethra for the withdrawal of urine from the urinary bladder comprising an elongated tubular flexible element having a pair of end portions, the first end portion constituting the leading end of the catheter which is introduced into the urinary bladder, one or more openings provided in said first end portion delivering urine from the urinary bladder into the tubular flexible element, the other end portion of said tubular flexible element constituting the trailing end of the catheter which is not insertable into the penis, and valve means provided between said end portions for opening and closing the tubular element to permit withdrawal of urine from the tubular element or collection of urine within the tubular element;

said flexible element extending through a support strap, said strap having a pair of arms, each arm having an adhesive surface for securing the arms to the penis to assist in preventing the accidental withdrawal of the tubular element from the penis and urethra;

said flexible element extends through the center portion of said support strap; and a medically treated disc surrounding the tubular element and engagable with the head of the penis for assisting in the prevention of infections in the human male;

said disc being a separate element which is separable from said support strap.

* * * * *